United States Patent [19]

Axelsson

[11] Patent Number: 4,895,515

[45] Date of Patent: Jan. 23, 1990

[54] DENTAL INSTRUMENTS

[75] Inventor: Per A. T. Axelsson, Hammarö, Sweden

[73] Assignee: Ingrid Margareta Axelsson et al., Sweden

[21] Appl. No.: 270,052

[22] Filed: Nov. 14, 1988

[30] Foreign Application Priority Data

Nov. 13, 1987 [SE] Sweden ............................ 8704435

[51] Int. Cl.⁴ .............................................. A61C 3/00
[52] U.S. Cl. .................................................... 433/166
[58] Field of Search ............... 433/165, 166, 118, 122, 433/123, 125, 143, 144

[56] References Cited

U.S. PATENT DOCUMENTS

1,712,469  5/1929  Force ................................. 433/122
3,552,022  1/1971  Axelsson ........................... 433/166
4,505,678  3/1985  Anderson .......................... 433/143
4,773,855  9/1988  Levy .................................. 433/118

Primary Examiner—Robert Peshock
Attorney, Agent, or Firm—Nixon & Vanderhye

[57] ABSTRACT

A dental instrument for cleaning and planing of tooth root faces comprises a conical or flattened working part, in which one or more countersunk grooves are cut out. Opposed side faces of said grooves form a sharp, essentially square-angled cutting edge with area of the working part situated on either side of the groove. When the deposits upon the tooth have been removed and the tooth face planed, said areas form load-relieving surfaces resting against the tooth face and preventing the cutting edges from coming into contact with and undesirably working off further undamaged tooth material.

12 Claims, 6 Drawing Sheets

DENTAL INSTRUMENTS

BACKGROUND AND SUMMARY OF THE INVENTION

This invention relates to dental instruments for removing calculus and plaque from teeth but which minimizes any significant removal of tooth material.

There are known in the art a variety of hand manipulable dental instruments for removing bacteria and calculus present on the root cementum portion of a tooth. Such instruments typically have sharply ground cutting edges which, during scraping, tend to remove good tooth material as well. In addition, these instruments require great skill on the part of the user in order to produce good results without also creating relatively deep scars in the dentine which can rapidly fill with undesirable microbes.

The present invention relates to a new design for dental instruments which substantially eliminates irregular removal of good tooth material while permitting effective removal of plaque and calculus.

More specifically, the present invention provides dental instruments which have axially spaced working surfaces separated by a recess or groove. The working surfaces and recess or groove surfaces combine to form substantially right right-angled cutting edges. The working surfaces themselves are substantially flat, forming load relieving surfaces which take up the pressure of the tool, and which prevent excess scraping action which would otherwise remove portions of the root cementum. Several exemplary embodiments of dental instruments incorporating this basic structure are described herein, in conjunction with the detailed description which follows.

DETAILED DESCRIPTION OF THE DRAWINGS

Figure 1A:
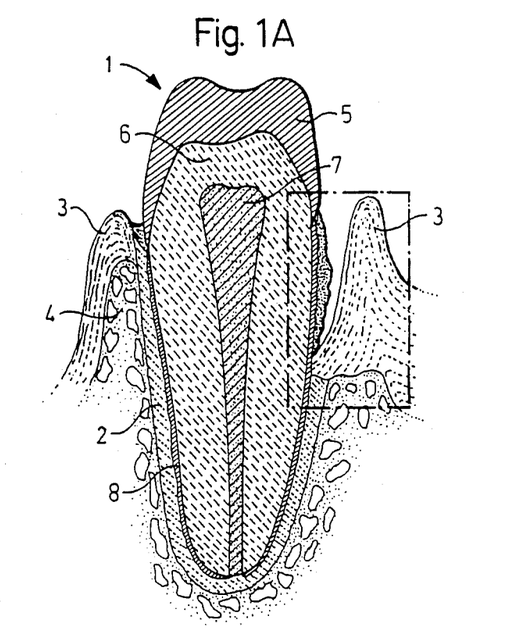
FIG. 1A is a cross-sectional view of a typical tooth structure.
Figure 1B:
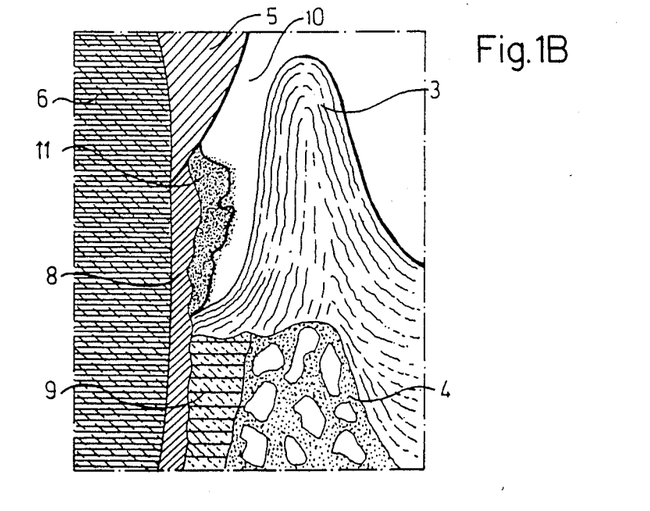
FIG. 1B is an enlarged view of the indicated area in FIG. 1.

Referring to FIGS. 1 and 2 of the drawings, a tooth consists of the visible crown 1 of the tooth, and the invisible root 2. The outer shell of the tooth crown is very hard and heavily mineralized, and comprises the tooth enamel 5. Beneath the tooth enamel there is a less heavily mineralized tissue 6, also known as dentine. The dentine is perforated by a great number of tubular passages extending from the inner vital tissue or pulp 7 of the tooth, to the enamel of the tooth crown and to the outer cover, or root cementum 8, of the root. The dentine tubules (not shown) are of a diameter of about 1 $\mu$m. They contain protrusions from living cells on the inner wall of the dentine. The dentine tubules are present in a number of about 10,000 per $mm^2$.

The pulp 7 consists of, among other things, blood vessels, nerves and different types of vital cells, and the root consists of the pulp 7 (the so-called root canal), the dentine 6, and the root cementum 8, the latter forming a protective cover for the root dentine and pulp.

The attachment of the root to the jaw comprises the gum or gingivae 3, the root cementum 8, the periodontal ligament 9 and the alveolar bone 4. In its sound state, the gingival margin is tightly adhered to the tooth surface as a tightly fitting sleeve. In the ligament 9 there are a great number of collagen fibres attached to the root cementum 8 and to the alveolar bone 4. The surface of the cementum 8 is extremely rough in order to enable attachment of an optimum number of root ligament fibres.

If microbes 11 are allowed to accumulate upon the tooth enamel 5 in contact with the gum margin 3 to form plaque, there arises a gingival inflammation (gingivitis). If the plaque is not removed in time, the attachment of the tooth to the jaw will be damaged. Specifically, the fibres of the root ligament 9 as well as the alveolar bone 4 begin to be destroyed directly or indirectly by the microbes 11 growing upon the tooth face or in its vicinity. The original site of the destructed root ligament is replaced by a spatula-shaped pocket between the root cementum 8 and the gum 3, i.e., a periodontal pocket 10 has been formed. Microbes 11 having spread from the comparatively smooth tooth enamel 5 to the rough root cementum 8 are now entrenched, as best seen in FIG. 1A. Due to the infectious periodontal inflammation (periodontitis), which now has resulted in partial loss of the attachment of the tooth, wound liquid (exudate) containing a great many minerals is let out into the periodontal pocket 10. These minerals are precipitated, and penetrate into the microbe incrustations upon the rough surface of the root cementum 8, so that calculus is formed thereon. According to research carried out by the inventor, it has been proved that the infectious inflammation (periodontitis) will be completely healed and further loss of periodontal attachment prevented, if the microbes and calculus attached to the rough root surface are thoroughly removed, and additional microbes are prevented from growing down into the periodontal pocket 10 by daily tooth cleaning.

Figure 2A:
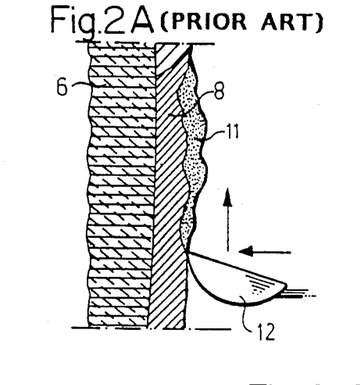
FIGS. 2A through 2E illustrate the manner of operation of prior art dental instruments on a tooth structure as disclosed in FIG. 1.
Figure 2B:
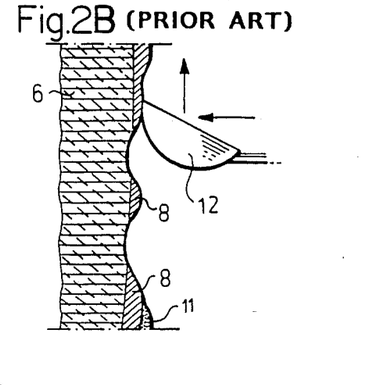
Figure 2C:
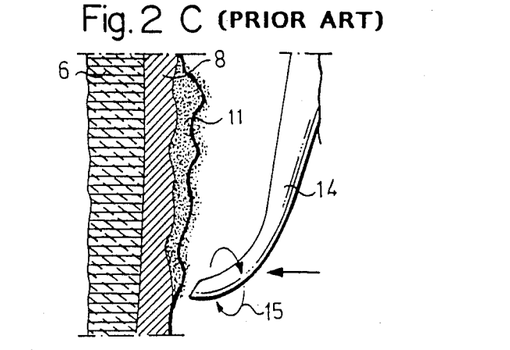

For complete removal of bacteria and calculus sticking to the surface of the root cementum 8, tools are required which reach down to the bottom of all rough areas. Most frequently hitherto, this has been done by the use of hand instruments having sharply ground cutting edges 12, e.g., double-ended currettes, as seen in FIGS. 2A and B. By simultaneously applying a contacting pressure of the cutting edge 12 of the instrument against the root cementum 8, and performing a combined planing and scraping movement from the bottom of the periodontal pocket 10 up towards its opening, the operator attempts to remove so much of the hard matter of the root surface as necessary to remove all calculus and microbe deposits as well. Direct observation deep into the periodontal pocket 10 is not possible during this type of treatment. Therefore, one has to rely entirely upon the tactile feeling which requires great experience as well as good manual skill in order to obtain the desired result. The root cementum 8 and the root dentine 6 are substantially of the same hardness and degree of mineralization. The thickness of the root cementum is merely 0.1 to 0.2 mm. Therefore, it is impossible to judge whether the whole of the protecting root cementum 8 is being removed and the tubules of the dentine 6 exposed, since the sharply ground instrument removes tooth material as long as pressure is applied during the scraping movement.

Figure 2D:
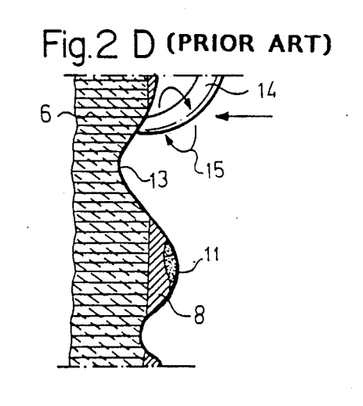
Figure 2E:
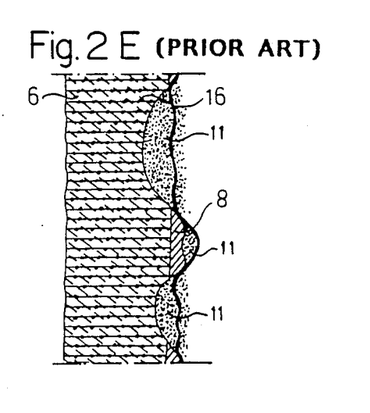

Such hand instruments require great manual skill. In frequent use of such instruments, the operator will also run the risk of joint infections. As a result, ultrasonic scaling instrument 14 have become a popular alternative. These can provide oval as well as reciprocating movements with a very short amplitude. The tactile feeling when using these instruments, however, is heavily reduced in comparison to the previously mentioned hand instruments. Results from recent research have shown that maximum power of the ultrasonic instruments must be used for removing most of the calculus and microbe depositions adhering to the rough root surface. At maximum power, the point of the ultrasonic instrument is difficult to control and can penetrate far into the dentine in random locations, as shown in FIG. 2D. The scars in the dentine caused by the instrument will very rapidly be filled up with microbes and calculus (FIG. 2E) if the patient does not clean his teeth regularly and meticulously As noted above, the diameter of the dentine tubules is about 1 μm. A great number of the kinds of microbes growing upon tooth surfaces are of a diameter of only 0.5 to 1 μm, so that microbes filling the scars in the dentine caused by the instrument can also migrate into the dentine tubules, as shown at 16 in FIG. 2E, and become inaccessible to further treatment by dental instruments. Therefore, after each renewed treatment, the root surface will be reinfected and prevent healing of the periodontitis. Moreover, microbes may also reach into the pulp 7 and cause toothache (pulpitis), requiring root-canal treatment. Considering these conditions, it is evident that more precise and safe instruments are required in order to achieve the best possible results from the treatment.

In order to solve the above-mentioned problems, in accordance with the present invention, a set of different instruments has been developed and tested. The basic idea has been to design the instruments so that removal of tooth material is prevented after the tooth surface is planed quite smooth and rid of calculus and dental plaque. The essential features of the instrument according to the invention, by which said object is reached, are set forth below.

Figure 3A:
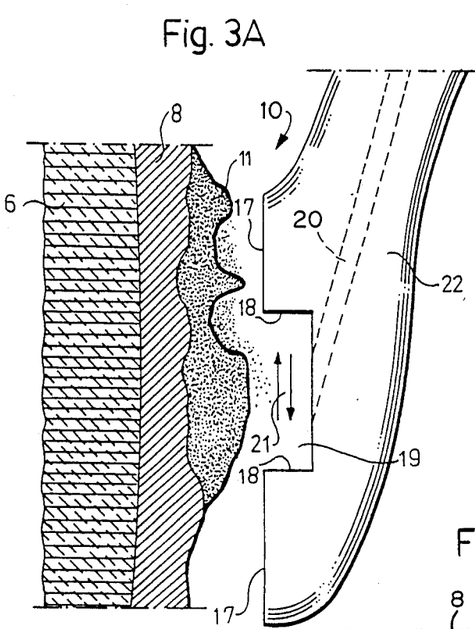
FIGS. 3A and 3B diagrammatically show an embodiment of the instrument according to the invention and its location along a tooth root surface before and after a finished treatment.
Figure 3B:
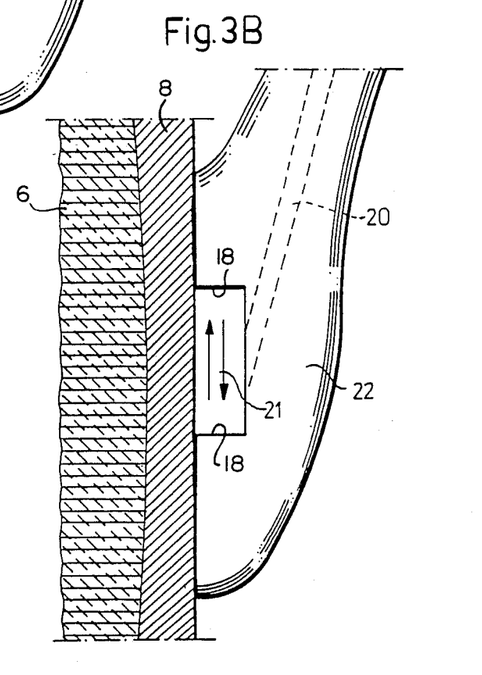

FIGS. 3A and 3B show on a magnified scale a portion of a tooth root and the working part of an instrument in accordance with this invention for cleaning and planing of the surface of the tooth root. Reference numerals used in FIGS. 1 and 2 are used in the remaining FIGURES to designate like tooth areas. Thus, numeral 6 designates the inner tissue of the tooth root, the dentine, and numeral 8 designates it outer cover, the root cementum Numeral 11 designates deposits, and partly in the form of plaque.

The instrument 22 inserted into the periodontal pocket 10 at the side of the tooth is so designed on its side facing the tooth, that the deposits 11 can be scraped off when reciprocatinq the instrument in the direction of the arrows 21, i.e., in the length direction of the tooth, but merely as long as it does not encounter any greater resistance when moved closer and closer to the tooth.

The working parts of the instrument are the essentially right-angled cutting edges formed between the opposed side walls 18 of a recessed groove 19 and the aligned surface areas 17, 17 on the side of the instrument facing the tooth. When the deposits have been loosened from the tooth surface and flushed off by flushing liquid supplied through a passage 20 provided in the instrument, and when the root cementum 8 has been planed, the surface parts 17, 17 will contact and rest against flat faces of the tooth and will form load-relieving surfaces taking up the pressure of the tool and keeping-back the cutting edges as best seen in FIG. 3B. In the continued use of the instrument, these surface parts 17, 17 of the instrument slide along the tooth surface, and the cutting edges will not perform any further scraping action to speak of, so that removal of root cementum to any significant degree and exposition of the dentine therebelow is prevented. Moreover, it will be much easier to get a well-polished and smooth root surface free of microbes and calculus, than in the case of root faces having deep defects in the dentine caused by the above described prior art scaling instruments.

The distance between the parallel cutting edges formed at the intersections of surface parts 17, 17 and groove side walls 18, 18, should preferably be of the order of 0.5 to 1.5 mm, and the depth of the groove 19 need not be more than 0.2 to 0.5 mm relative to the surface parts 17, 17. The opposed side walls 18, 18 of the groove, if desired, may be undercut in order to reduce the edge angle which, preferably, is from about 70 to about 90 degrees.

The groove 19 extends transversely across the instrument, i.e., at right angles to the plane of the paper, and has an extension and curvature depending upon the design of the various embodiments as described below. In this regard, FIG. 3 serves primarily to explain the basic idea and concept of the invention. For ease of understanding, surfaces corresponding to surface parts 17 and groove 19 are designated by like numerals in the exemplary embodiments described further below.

Figure 4A:
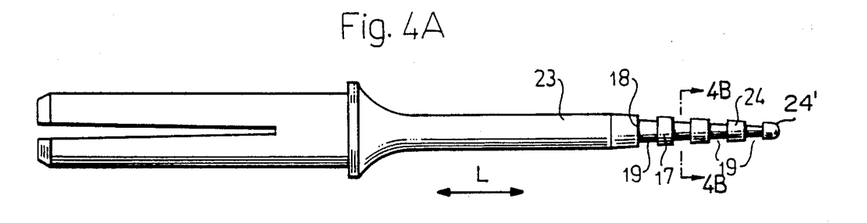
FIG. 4A is a side view of an instrument in accordance with a first exemplary embodiment of the invention.
Figure 4B:
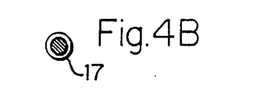
FIG. 4B is a cross-sectional view taken along the line B—B in FIG. 4A.

In the exemplary embodiment shown in FIGS. 4A and 4B, an instrument in accordance with the invention consists of a conical working tip 24 made integral with a preferably cylindrical shaft 23. In a manner not shown, the shaft is connected to a holder driven by a motor which imparts to the instrument a rapid reciprocating movement in the length direction L, with an amplitude of the order of 0.5 to 2 mm. One suitable motor is described in U.S. Pat. No. 3,552,022. The working tip 24, having a cone angle of 10 to 20 degrees, terminates with a spherically rounded extreme end point 24'. Cut out of the conical face 17 of the working tip are four circumferential grooves 19 of a uniform cross-section and of the contour shown in FIGS. 3A and 3B. The bottom face of the groove may be conical or cylindrical, and its two opposed lateral faces 18 take the shape of circular rings or annulets. On account of the conicity (taper) of the base of the grooves, one cutting edge will get an edge angle somewhat less than 90 degrees, whereas the angle of the opposed edge will be slightly greater than 90 degrees.

Figures 10, 11, 12A, 12B, 13A, 13B:
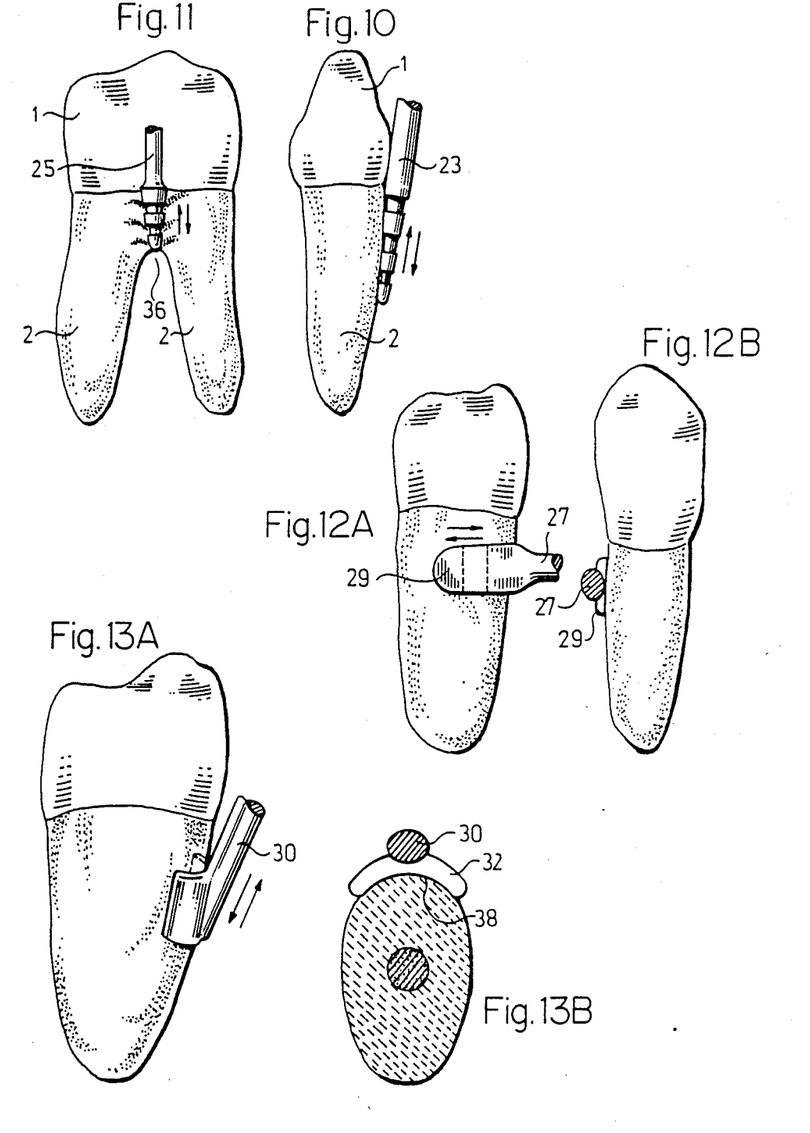
FIG. 10 shows the instrument of FIGS. 4A and 4B in use upon an incisor tooth.
FIG. 11 shows the instrument of FIG. 5 in use upon a molar.
FIGS. 12A and 12B show two views of the instrument of FIGS. 6A through 6C in use, taken at right angles to each other.
FIGS. 13A and 13B are front and cross-sectional end views of the instrument of FIGS. 7A through 7C in use.

It is important that the load-relieving surface parts 17, 17 on either side of the grooves 19 coincide with one and the same conical surface, so that the cutting edges cannot work upon the tooth after said areas 17 having come into contact with the smoothed face of the tooth. The embodiment of FIGS. 4A, 4B is suitable for use in the treatment of various parts of the roots 2, as illustrated in FIG. 10.

Figure 5:
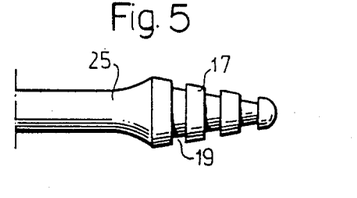
FIG. 5 is a partial side view of a variation of the instrument illustrated in FIG. 4A.

The embodiment of FIG. 5 has a conical tip, the peripheral surface parts 17 of which taper gradually with an increasing angle towards the end. Three circumferential grooves 19 are cut out of said face. The remainder of this design is essentially similar to that of FIGS. 4A and 4B. This embodiment is suitable for being used vertically on the concave faces formed at the bifurcation 36 between roots 2 of a molar tooth as illustrated in FIG. 11.

Figure 6A:
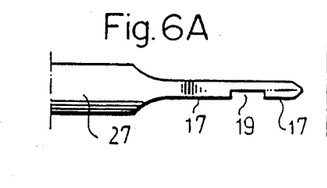
FIGS. 6A through 6C are partial side, bottom and end views, respectively of a third exemplary embodiment of the invention.
Figure 6B:
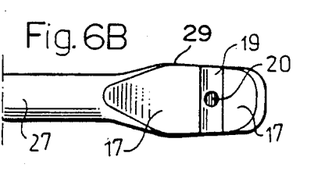
Figure 6C:
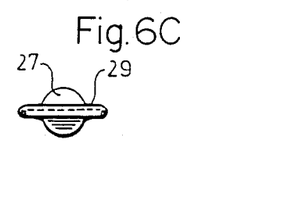

In the embodiment of FIGS. 6A-6C, the end of the shaft 27 merges into a wider, flattened part 29, the front side of which forms the flat load-relieving parts 17, 17 and the back side being convexly rounded. The groove 19 extends transversely across the front side of the working part and forms a free space between the two parts 17, 17 of the load-relieving element. In said space the loosened particles may be collected before they are flushed out by the water supplied through the passage 20. The described embodiment is suitable for use in the treatment of flat or slightly curved root faces located close to adjacent teeth illustrated in FIGS. 12A and 12B, and can work there horizontally as well as diagonally.

Figure 7A:
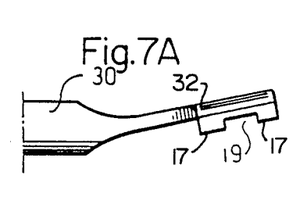
FIGS. 7A through 7C are partial side, bottom and end views, respectively of a fourth exemplary embodiment of the invention.
Figures 7B, 7C:
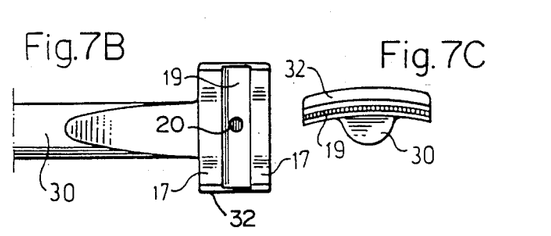

In the embodiment of FIGS. 7A-7C, the shaft 30 merges into a flattened working part 32 which is considerably wider than part 29 in FIGS. 6A-6C and, in addition, is provided with a working face having a concave or cup-shaped curvature, best seen in FIG. 7C. The groove 19 separating the surface parts 17, 17 of the load-relieving element are arcuate and extend over the entire width of the working face, so that supplied flushing liquid and entrained particles can depart through the open ends of the groove 19. The described embodiment is particularly suitable for the use in the treatment of a tooth having a surface 38 of a convex cross-section, as illustrated in FIGS. 13A, 13B. The instrument is driven with a reciprocating movement in the vertical direction, i.e., in the length direction of the tooth.

Figure 8A:
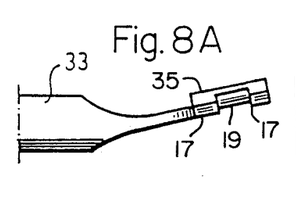
FIGS. 8A through 8C are partial side, bottom and end views, respectively, of a fifth exemplary embodiment of the invention.
Figures 8B, 8C:
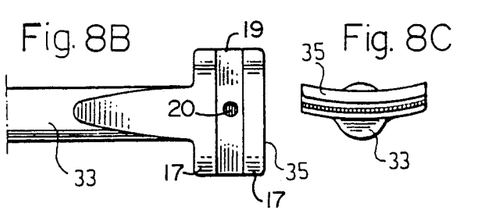
Figure 14:
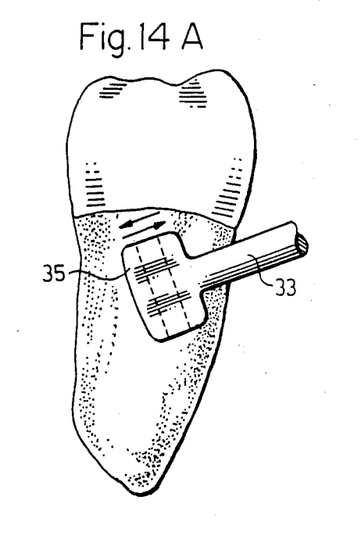
FIGS. 14A and 14B are front and cross-sectional end views of the instrument of FIGS. 8A through 8C in use.

The embodiment of FIGS. 8A-8C differs from that shown in FIGS. 7A-7C merely in that the working surface 35, merged with the shaft 33, is curved in the opposite direction, i.e., is convex towards the tooth surface, and therefore suitable for treatment of such concave root surfaces 39 as are common close to adjacent teeth, as illustrated in FIGS. 14A, 14B. The working surface is convexly curved not only in the transverse direction but also in the length direction, and can therefore be driven horizontally as well as diagonally across the tooth surface.

Figure 9A:
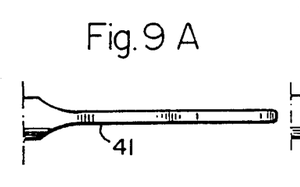
FIGS. 9A through 9C are partial side, bottom and end views, respectively, of a sixth exemplary embodiment of the invention.
Figures 9B, 9C:
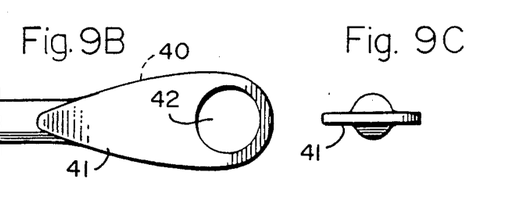

The embodiment of FIGS. 9A-9C differs from the rest in that the working edges 40 form a closed circular or oval-shaped line around a central recess in the flat end part 41 of the instrument, and in that the recess, instead of being in the shape of an open-ended straight or curved groove, takes the shape of a bottomed or through hole 42. The opposite cutting edge parts are symmetrical about a center line and may be curved, as shown, or almost straight or parallel over a greater part.

In most of the above-described embodiments, the instrument is provided with an interior tubular passage 20 ending in the bottom face or base of the groove 19. The passage serves to supply germicidal irrigating liquid with the objective of removing and killing infectious matter in the periodontal pocket 10 which has been mechanically loosened from the root surface.

Figure 15A:
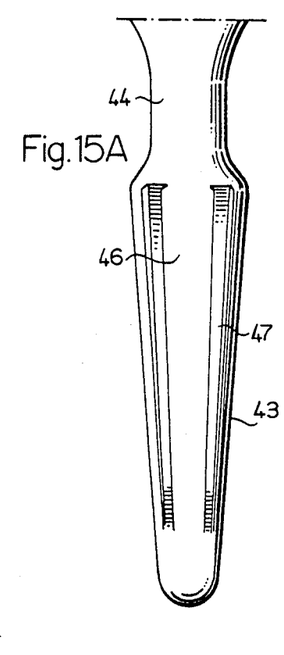
FIGS. 15A through 15C show two variants of a seventh exemplary embodiment, viewed from the side and from the end.
Figure 15B:
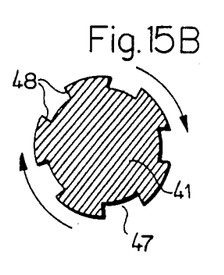
Figure 15C:
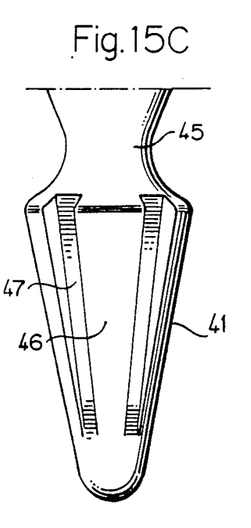

The invention may also be applied to rotary tooth cleaning instruments. FIGS. 15A-15C show two variants which differ merely in respect of length and conicity. The working part 43, which is united with the shaft 44 and 45, respectively, has an exterior surface 46 of a conicity which is either uniform or varies somewhat along the length. Cut out of said surface are grooves 47 which extend in the length direction of the instrument at a mutual distance gradually diminishing towards the end. The surface parts remaining between the grooves form load-relieving areas, which during the rotation of the instrument and after the removal of the deposits, slide along and rest against the treated tooth surface, so that the sharp edges at the sides 48 of the grooves are prevented from working upon the already planed tooth surfaces.

With the scope of the following claims the described embodiments may, of course, be modified in respect of details, such as the number of grooves, dimensions, profiles, etc.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A dental instrument for planing tooth surfaces to remove calculus and plaque comprising:
   a shaft, one end of which is adapted to be attached to an driven by a driving means, and a working part formed at the other end of said shaft and adapted to work upon tooth surfaces in the mouth of a patient, said working part including at least a pair of axially spaced, substantially flat surface parts separated by a recessed area, said area defined in part by opposed surfaces which intersect said axially spaced surface parts at substantially 90° to form opposed cutting edges on opposite sides of said recessed area, said axially spaced, substantially flat surface parts substantially preventing removal of tooth material, including root cementum and dentine, once the tooth surfaces have been planed smooth.

2. An instrument as defined in claim 1 wherein said recessed area lies substantially transverse to a longitudinal axis of said shaft.

3. An instrument as defined in claim 1 wherein said recess comprises a groove having a bottom wall connecting said opposed surfaces.

4. An instrument as claimed in claim 3, wherein said working part is conically tapered, and said groove extends circumferentially around said working part.

5. An instrument as claimed in claim 3 wherein the working part has a flattened side, and said groove opens onto said flattened side and extends across said flattened side in opposite directions.

6. An instrument as claimed in claim 2, wherein the working part has a flattened and concavely curved surface, across the entire width of which there extends said recessed area in the form of a countersunk groove.

7. An instrument as claimed in claim 2, wherein the working part has a flattened and convexly curved surface, across the entire width of which there extends said recessed area in the form of a countersunk groove.

8. An instrument as claimed in claim 1 and wherein the working part is conical and is shaped with a plurality of axially spaced annular grooves.

9. An instrument as claimed in claim 3 and further including a tubular passage for supplying irrigating liquid, said passage terminating in the bottom of wall said groove.

10. An instrument as defined in claim 3 wherein said groove has a width of about 0.5 to about 1.5 mm and a depth of about 0.2 to about 0.5 mm.

11. A dental instrument for removing calculus and plaque from teeth comprising a shaft, one end of which is adapted to be driven by a driving means, and a working part formed at the other end of said shaft and adapted to work upon tooth surfaces in the mouth of a patient, said wörking part being provided with sharp cutting edges of a square cross-section situated at opposite sides of a recess therein, one side of each edge being collateral with the flat or curved side of said working part and the other side of the edge being substantially perpendicular thereto, said working part associated with each edge comprising means for substantially preventing removal of tooth material, including root cementation and dentine, when said surfaces come into contact with a smoothed face of the tooth.

12. An instrument as defined in claim 1, wherein said recess comprises a single straight longitudinal groove of a uniform cross-section extending substantially transverse to the axis of the shaft and having a bottom wall connecting said opposed surfaces.

* * * * *